United States Patent [19]
King

[11] Patent Number: 5,591,647
[45] Date of Patent: Jan. 7, 1997

[54] ANALYTE DETECTION BY COMPETITIVE INHIBITION OF ION CHANNEL GATING

[75] Inventor: Lionel G. King, North Ryde, Australia

[73] Assignees: Australian Membrane and Biotechnology Research Institute, Homebush; The University of Sydney, Sydney, both of Australia

[21] Appl. No.: 436,236

[22] PCT Filed: Dec. 2, 1993

[86] PCT No.: PCT/AU93/00620

§ 371 Date: May 17, 1995

§ 102(e) Date: May 17, 1995

[87] PCT Pub. No.: WO94/12875

PCT Pub. Date: Jun. 9, 1994

[30] Foreign Application Priority Data

Dec. 3, 1992 [AU] Australia .................. 6171

[51] Int. Cl.⁶ ........................................... G01N 33/543
[52] U.S. Cl. ........................ 436/518; 436/525; 436/528; 436/532; 436/806; 435/7.2; 435/7.5; 422/82.02; 210/500.27
[58] Field of Search ................... 204/403, 415, 204/416, 418; 422/82.01–82.03; 435/817, 291, 317.1, 7.5, 7.2; 436/501, 518, 519, 524, 525, 527, 532, 806, 829, 528; 210/500.27

[56] References Cited

U.S. PATENT DOCUMENTS

| | | |
|---|---|---|
| 5,168,057 | 12/1992 | Oh et al. . |
| 5,436,170 | 7/1995 | Cornell et al. . |

FOREIGN PATENT DOCUMENTS

| | | |
|---|---|---|
| 21279/88 | 3/1989 | Australia . |
| 50334/90 | 8/1990 | Australia . |
| 2195450A | 4/1988 | United Kingdom . |

Primary Examiner—James C. Housel
Assistant Examiner—Prasad A. Murthy
Attorney, Agent, or Firm—Nixon & Vanderhye

[57] ABSTRACT

Membrane for use in the detection of an analyte having a closely packed array of self-assembling amphiphilic molecules and a plurality of ionophores. First and second ligands are attached to an end of the ionophores adjacent the surface of the membrane. The membrane is such that the binding of the first ligand to its specific binding partner prevents the flow of ions across the membrane via the ionophores. In addition, the binding of the second ligand to its specific binding partner prevents the binding of the first ligand to its specific binding partner.

4 Claims, 4 Drawing Sheets

ANALYTE DETECTION BY COMPETITIVE INHIBITION OF ION CHANNEL GATING

The present invention relates to a membrane incorporating ionophores the conductance of which may be gated.

BACKGROUND OF THE INVENTION

The concept of membranes incorporating ionophores, the conductance of which are gated and the use of such membrane in biosensors is disclosed in International patent application Nos WO89/01159, WO90/08783, PCT/AU89/00352, PCT/AU92/00132 and PCT/AU93/00509. The disclosure of each of these documents is incorporated herein by reference.

The present invention stems from an observation made by the present inventor during the work conducted and disclosed in International application No WO90/08783. In this earlier application it was shown that the conduction of biotinylated gramicidin ion channels in a lipid membrane is greatly reduced by the binding of streptavidin by the biotins attached to the gramicidin, and that the changing conduction in this system is directly related to the quantity of streptavidin bound to the membrane ion channels. From this observation the present inventor has developed a general mechanism for analyte detection using a membrane incorporating ionophores.

DESCRIPTION OF THE INVENTION

Accordingly, in a first aspect the present invention consists in a membrane for use in the detection of an analyte, the membrane comprising a closely packed array of self-assembling amphiphilic molecules, a plurality of ionophores and a first and a second ligand attached to an end of the ionophore adjacent the surface of the membrane, characterised in that the binding of the first ligand to its binding partner prevents the flow of ions across the membrane via the ionophores and in that binding of the second ligand to its binding partner prevents the binding of the first ligand to its binding partner.

In a preferred embodiment of the present invention the first ligand is biotin, the binding partner of which is streptavidin.

In a further preferred embodiment of the present invention the ionophores are gramicidin or gramicidin analogues.

Typically, the second ligand is the analyte which the membrane is to be used for detecting. It is, however, possible that the second ligand may vary from ionophore to ionophore. In this manner the membrane could be used to detect the presence of more than one analyte.

BRIEF DESCRIPTION OF THE DRAWINGS

In order that the nature of the present invention may be more clearly understood the operation of the membrane of the present invention will be described with reference to the following schematic representations of the operation of the gating mechanism, in which.

DETAILED DESCRIPTION OF THE INVENTION

Figure 1:
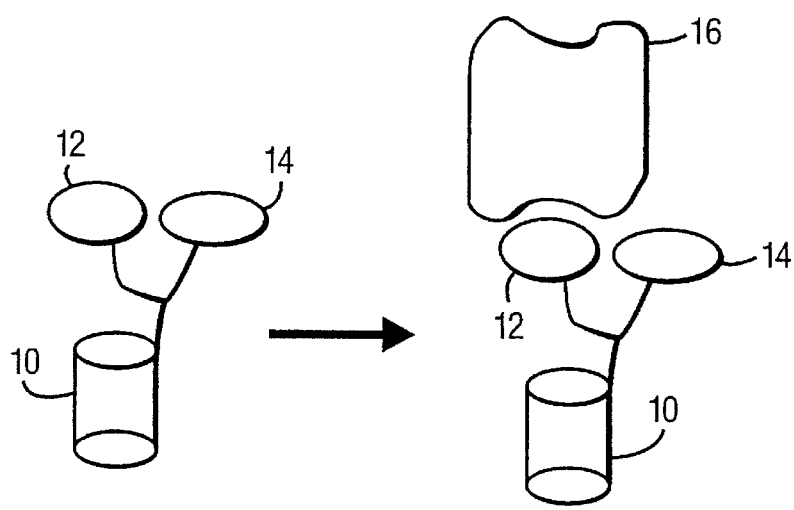
FIG. 1 is a schematic representation of a modified gramicidin ion channel with two ligands attached to the channel.

FIG. 1 shows a modified gramicidin ion channel (10) with two ligands (12 and 14) attached to the C terminus of the channel (10). One ligand (12) is biotin and is capable of binding streptavidin (16) so as to reduce the gramicidin (10) conductance. The second ligand (14), connected in close proximity to the biotin ligand (12), is the analyte of interest, an epitopic portion of the analyte, a structural analogue of either of the above or any ligand capable of competitively binding with an antibody raised against the analyte. In the absence of any species binding to the second ligand (14), binding of streptavidin (16) to the biotin ligand (12) effects a gating of the channel (10).

Figure 2:
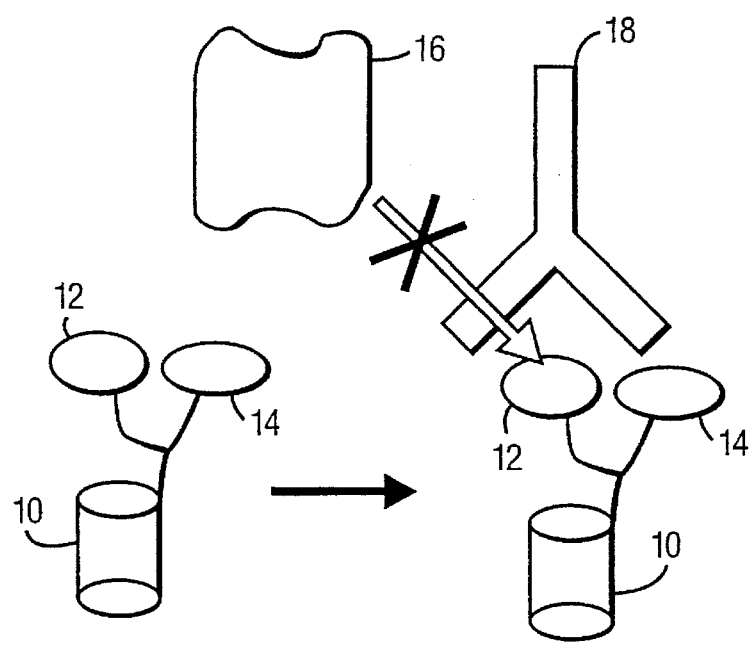
FIG. 2 is a schematic representation of the effect of adding anti-analyte antibody to the arrangement shown in FIG. 1.

FIG. 2 demonstrates the effect of adding an anti-analyte antibody (18) to the system described above. Attachment of the antibody (18) to the second ligand (14), while not of itself effecting the conductance of channel (10), sterically precludes binding of streptavidin (16) to the biotin ligand (12). As many channels (10) as have bound antibody (18) are, therefore, unable to be gated.

Figure 3:
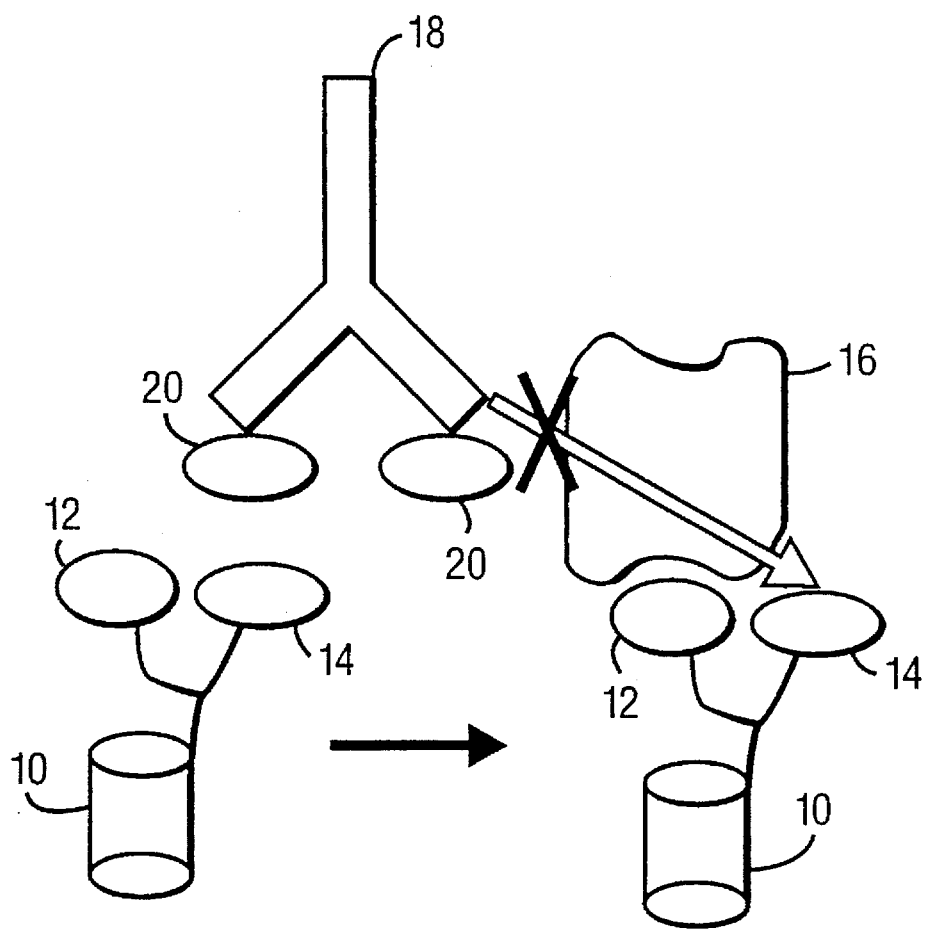
FIG. 3 is a schematic representation of the use of the system shown in FIG. 1.

The use of this system to measure analyte concentrations is illustrated in FIG. 3. In the presence of free analyte (20) in the sample solution, anti-analyte antibody (18) antigen binding sites will be occupied by the solution analyte (20), in proportion to the analyte concentration. These antibodies (18) will be prevented from binding to the second ligand (14) on the ion channel (10), leaving a fraction of ion channels (10) available for gating by streptavidin (16) in proportion to the amount of analyte (20) present in the sample solution. The amplitude of the channel (10) gating will therefore reflect the analyte (20) concentration.

EXAMPLE

In order that the nature of the present invention may be more clearly understood a preferred form thereof will now be described with reference to the following example.

EXAMPLE

Preparation of gramicidin
N-epsilon-(2,4-dinitrophenyl)-N-alpha-(N-biotinyl)-6-amino-caproyl)lysine ester (GaKDXB)

A mixture of gramicidin D (Sigma, 105 mg), N-alpha-BOC-N-epsilon-benzyloxycarbonyllysine (207 mg), dicyclohexylcarbodiimide (127 mg) and 4-(N,N-dimethylamino)pyridine (11 mg) in dry dichloromethane (30 ml) was heated under reflux for 2 hours then stirred at room temperature overnight. The mixture was then filtered, evaporated to dryness and chromatographed on a silica gel column eluted with dichloromethane/methanol/water/acetic acid (400:50:4:1) thence (400:60:6). The Ehrlich's reagent active fractions were combined and evaporated to dryness. The residue was dissolved in mixture of dichloromethane (5 ml), methanol (5 ml), water (0.1 ml) and acetic acid (0.1 ml) and stirred with 10% palladium on charcoal (100 mg) under an atmosphere of hydrogen for 3 days. The mixture was filtered, evaporated no dryness and chromatographed on a silica gel column eluted with dichloromethane/methanol/water (400:50:4) thence (400:60:6) to afford a polar, Ehrlich's agent reactive fraction of gramicidin N-alpha-BOC-lysine ester (78mg).

A solution of gramicidin N-alpha-BOClysine ester (78 mg) in a mixture of dichloromethane (4 ml) and methanol (2 ml) was treated with 2,4-dinitrofluorobenzene (50 µl). The mixture was stirred for 2 hours then evaporated to dryness. The residue was chromatographed on silica gel eluted with methanol/dichloromethane (5:95, 150 ml) thence dichloromethane/methanol/water (400/40/4), (200 ml) the front-running yellow fractions which were eluted with dichloromethane/methanol/water were combined and evaporated to dryness to afford gramicidin N-alpha-BOC-N-epsilon-2, 4-dinitrophenyllysine ester (34 mg).

A solution of gramicidin N-alpha-BOC-N-epsilon-2,4-dinitrophenyl lysine ester (18 mg) was dissolved in trifluoroacetic acid (3 ml) and stirred for 3 minutes then the solution was evaporated to dryness. The residue was layered with toluene (5 ml) and evaporated to dryness (process was repeated 3 times). The residue was taken up in a mixture of dichloromethane (4 ml) and methanol (2 ml) and the mixture was adjusted to pH 9 with triethylamine. N-Biotinyl-6-aminocaproic acid N-hydroxysuccinimide ester (10 mg) was then added to the solution and the mixture was stirred at room temperature overnight. The mixture was then evaporated to dryness then chromatographed on a silica column eluted with dichloromethane/methanol (95:5, 150 ml) then dichloromethane/methanol/water (400:40:4,200 ml). The first three (yellow) fractions eluted with dichloromethane/methanol/water solvent mixture were combined and evaporated to dryness to afford a yellow powder of gramicidin N-epsilon-2,4-dinitrophenyl-N-alpha(N-biotinyl-6-aminocaproyl)lysine ester (34 mg).

Construction of Membrane

Figure 5:
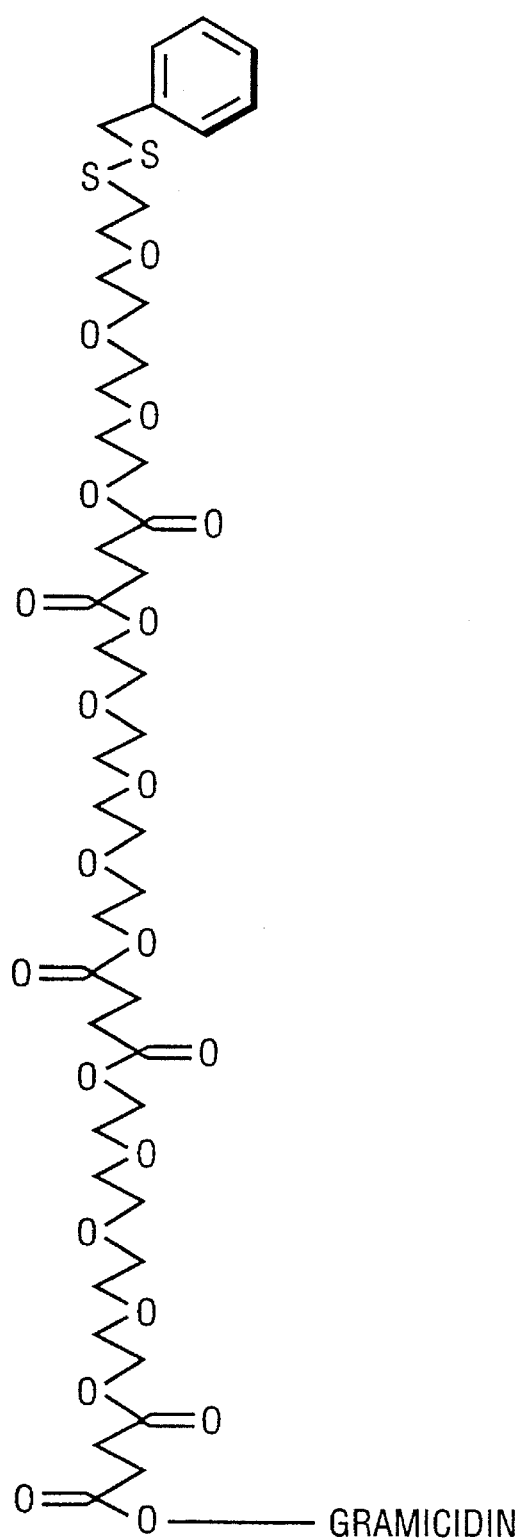
FIG. 5 is a representation of gramicidin B.

Over a freshly evaporated gold electrode (2 mm$^2$ area) on a glass substrate was placed an open-ended cylindrical teflon sleeve (4 mm in diameter, 10 mm high). The teflon sleeve was secured in position by a metal clamp to create a tight seal at the glass-teflon interface. A solution of glycerol monooleate (140 mM), reservoir lipid A (23-(20'-Oxo-19'-oxaeicosa-(Z)-9'-ene)-70-phenyl-20,25,28,42,45-pentaoxo-24-aza-19,29,32,35,38,41,46,47,52,55-decaox a-58,59-dithiahexaconta-(Z)-9-ene, described in detail in PCT/AU93/00509) (140 μM) and gramicidin B (shown in FIG. 5 and described in greater detail in PCT/AU93/00509) (1.4 μM) in a mixture of tetradecane and ethanol (1:9) (2 μl) was placed in the teflon well assembly, followed immediately by a solution of sodium chloride (0.1M, 100 μl). The assembly was then allowed to stand overnight. The aqueous solution was then removed by syringe and the well was washed with water (100 μl) thence ethanol (3×100 μl). The assembly was allowed to dry then a solution of glycerolmonooleate (140 mM) and gramicidin N-epsilon-2,4-dinitrophenyl-N-alpha-(N-biotinyl-6-amino-caproyl)lysine ester (14 μM) in a mixture of tetradecane and ethanol (1:9, 5 μl) was added. A solution of sodium chloride (0.1M, 100 μl) was immediately added to the well and the well was then purged with 5×100 μl volumes of 0.1M sodium chloride. The membrane assembly was then allowed to stand under a 100 μl volume of 0.1M sodium chloride overnight.

Assay of 2,4-dinitroaniline

A commercial preparation of rabbit anti-dinitrophenyl (DNP) antibody (Dakopatt, 7 mg/ml total antisera) was diluted 1:10 into 0.1M sodium chloride solution. A series of samples were then prepared containing 90 μl of the 1:10 dilution of anti-DNP antibody and 10 μl of a solution of 2,4-dinitroaniline in water which had been acidified to pH 4.5 with HCl. The final concentration of 2,4-dinitroaniline in the solution ranged from 25 μM to 1 μM in twofold serial dilutions. The solutions were allowed to stand overnight.

Figure 4:
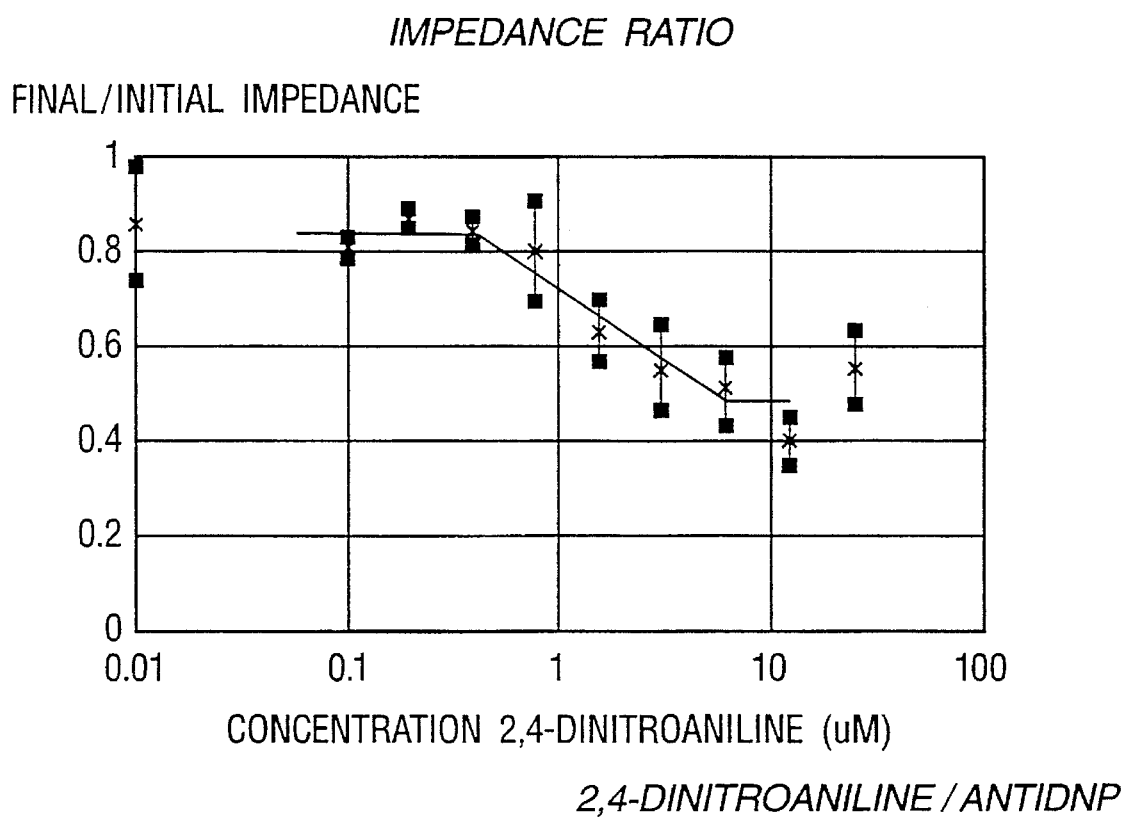
FIG. 4 is a graph of final/initial impedance against concentration of 2,4-dinitroanaline.

Sets of three sensor membranes for each 2,4-dinitroaniline concentration, prepared as described above and monitored by AC impedance spectroscopy, were treated with a 2,4-dinitroaniline-antiDNP antibody solution (5 μl). After 10 minutes a solution of streptavidin (0.5 mg/ml, 2 μl) was added. The ratio of the AC impedance values immediately before and 5 minutes after streptavidin addition at the frequency giving the largest impedance response to streptavidin was proportional to the amount of 2,4-dinitroaniline present in the initial sample added to the membrane (FIG. 4).

It is disclosed in co-pending International Patent Application No. PCT/AU93/00509 that advantages may be achieved by the exclusion of tetradecane in the preparation of membrane bilayers. It is not clear at this point, however, whether any advantage will be gained in the present system by the exclusion of tetradecane from the membrane solutions.

As will be readily understood by persons skilled in the art the first and second ligands may be any of a large number of such binding molecules well known in the art. There is, however, the requirement that the second ligand is not so large that it prevents the binding of the first ligand to its binding partner even in the absence of the second ligand binding to its binding partner. Of course, in such a situation, there would be no meaningful gating of the ion channels.

As stated above the gating mechanism of the present invention is not restricted to inhibition of streptavidin-biotinylated gramicidin gating. Any gating process which can be interfered with sterically will be amenable to this approach. For example it could be envisaged that the gating of gramicidin ion channels could be effected by the cross-linking of adjacent gramicidin ion channels via the first ligand. In this example the first ligand could include a group which under oxidative conditions could cross-link with a corresponding group on an adjacent gramicidin residue thereby preventing the ions across the membrane via the gramicidin ion channels. The binding of the second ligand to its binding partner could then prevent the cross-linking and concomitant gating and, by analogy, to the biotin-streptavidin example above, provide another general detection scheme.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A membrane for use in the detection of an analyte, the membrane comprising a closely packed array of self-assembling amphiphilic molecules, a plurality of ionophores and a first and a second ligand attached to an end of the ionophore adjacent the surface of the membrane, wherein the binding of the first ligand to its specific binding partner prevents the flow of ions across the membrane via the ionophores and wherein binding of the second ligand to its specific binding partner prevents the binding of the first ligand to its specific binding partner.

2. A membrane as claimed in claim 1 in which the first ligand is biotin.

3. A membrane as claimed in claim 1 in which the ionophores are gramicidin or gramicidin analogues.

4. A membrane as claimed in claim 2 in which the ionophores are gramicidin or gramicidin analogs.

* * * * *